(12) United States Patent
Okamoto et al.

(10) Patent No.: US 9,784,709 B2
(45) Date of Patent: Oct. 10, 2017

(54) SENSOR ELECTRODE, MANUFACTURING METHOD THEREOF, AND METAL PASTE FOR ELECTRODE FORMATION

(71) Applicant: Tanaka Kikinzoku Kogyo K.K., Chiyoda-ku (JP)

(72) Inventors: Nobuhisa Okamoto, Hiratsuka (JP); Takuya Hosoi, Hiratsuka (JP); Koichi Sakairi, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 118 days.

(21) Appl. No.: 14/430,235

(22) PCT Filed: Sep. 17, 2013

(86) PCT No.: PCT/JP2013/074970
§ 371 (c)(1),
(2) Date: Mar. 23, 2015

(87) PCT Pub. No.: WO2014/050624
PCT Pub. Date: Apr. 3, 2014

(65) Prior Publication Data
US 2015/0241384 A1    Aug. 27, 2015

(30) Foreign Application Priority Data

Sep. 25, 2012 (JP) .................................. 2012-210527

(51) Int. Cl.
*G01N 27/407* (2006.01)
*H01B 1/22* (2006.01)
(Continued)

(52) U.S. Cl.
CPC .......... *G01N 27/4075* (2013.01); *C09D 5/24* (2013.01); *G01N 27/304* (2013.01); *H01B 1/22* (2013.01); *H01B 13/0016* (2013.01)

(58) Field of Classification Search
None
See application file for complete search history.

(56) References Cited

U.S. PATENT DOCUMENTS

| 4,946,577 A | 8/1990 | Shibata |
| 2004/0050692 A1 | 3/2004 | Lehmann et al. |

(Continued)

FOREIGN PATENT DOCUMENTS

| DE | 102009028755 A1 | 6/2011 |
| DE | 10 2010 001 567.9 A1 | 8/2011 |

(Continued)

OTHER PUBLICATIONS

English translation of DE 102009028755 A1.*
(Continued)

*Primary Examiner* — J. Christopher Ball
(74) *Attorney, Agent, or Firm* — Orrick, Herrington & Sutcliffe, LLP; Joseph Calvaruso

(57) ABSTRACT

The present invention relates to a gas sensor electrode including a conductive particle phase made of Pt or Pt alloy and a ceramic particle phase being mixed and dispersed, wherein a rate of content of the ceramic particle phase is 6.0 to 22.0 mass %, and a void ratio is 2.5 to 10.0%, and a dispersion degree of the conductive particle phase per length of 25 μm on the electrode surface is 0.60 to 0.85 μm, and a dispersion degree of the conductive particle phase in the electrode cross section per length of 100 μm in a direction parallel to the electrode surface is 2.0 to 4.0 μm. This electrode can be produced by firing a metal paste made by dispersing, in a solvent, a conductive particle having a core/shell structure in which a core particle such as Pt is covered with a ceramic shell and ceramic powder. The gas sensor electrode according to the present invention has a high electrode activity.

15 Claims, 4 Drawing Sheets

(51) Int. Cl.
    *C09D 5/24* (2006.01)
    *G01N 27/30* (2006.01)
    *H01B 13/00* (2006.01)

(56) References Cited

U.S. PATENT DOCUMENTS

| | | |
|---|---|---|
| 2006/0231397 A1 | 10/2006 | Nakagaki et al. |
| 2007/0084723 A1 | 4/2007 | Mizutani et al. |
| 2012/0061231 A1 | 3/2012 | Kobayashi et al. |
| 2012/0126183 A1* | 5/2012 | Hosoi .................. H01B 1/02 252/514 |

FOREIGN PATENT DOCUMENTS

| | | |
|---|---|---|
| EP | 0059933 A1 | 9/1982 |
| JP | 59-142457 A | 8/1984 |
| JP | 1-176937 A | 7/1989 |
| JP | 10-48175 A | 2/1998 |
| JP | 2000-12042 A | 1/2000 |
| JP | 2001-74685 A | 3/2001 |
| JP | 2005-283240 A | 10/2005 |
| JP | 4834170 B1 | 12/2011 |

OTHER PUBLICATIONS

European Search Report 13840644.2, for PCT/JP2013/074970, dated Mar. 21, 2016.
Extended European search report, including supplementary European search report and European search opinion, reference 59901PEPWO, Application No./Patent No. 13840644.2-1554 / 2902775 PCT/JP2013074970, dated Jun. 30, 2016.
International Search Report PCT/JP2013/074970, dated Dec. 10, 2013.
European Search Report for EP appl. 171539513, dated Apr. 24, 2017.

* cited by examiner

SENSOR ELECTRODE, MANUFACTURING METHOD THEREOF, AND METAL PASTE FOR ELECTRODE FORMATION

TECHNICAL FIELD

The present invention relates to a gas sensor electrode constituting a sensitive unit of a gas sensor such as an oxygen sensor and an NOx sensor, and further, to a method of manufacturing the same and a metal paste for forming an electrode.

BACKGROUND ART

A fired metal paste has been conventionally used as electrodes constituting gas sensor electrodes and heater electrodes of various kinds of gas sensors such as an oxygen sensor, an NOx sensor, and an exhaust temperature sensor. The reason why a metal paste is applied to production of these electrodes is because the metal paste can cope with complicated electrode patterns, and in addition, a substrate and an electrode can be produced simultaneously by applying and firing a metal paste on a green sheet forming a ceramic substrate, and this is preferable from the perspective of the production efficiency.

A known configuration of a metal paste for forming an electrode includes a mixture obtained by mixing conductive particles such as precious metal and ceramic powder such as $Al_2O_3$ or $ZrO_2$ into a solvent. The reason why ceramic powder is mixed into the metal paste is because, when a substrate and an electrode are produced at a time by applying and firing the metal paste to the green sheet as described above, a difference in the shrinkage rate between the metal paste and the green sheet is corrected, the problem of warping and deformation of the substrate is solved, and the adhering property of the electrode is improved. In fact, the ceramic powder ensures the formation property of an electrode film, but on the other hand, there is a disadvantage in that the resistance value of the produced electrode film is increased to a higher level than an electrode of a bulk metal. For this reason, when the ceramic powder is used, it is a problem to study the optimum usage mode and mixing amounts while achieving the balance between ensuring of the formation property and the resistance reduction of the electrode.

In association with the above problem, the present inventors disclose a metal paste that can produce a low resistance electrode film and has superior adhering property and adapting property to a substrate and an electrode produced thereby (Patent Document 1). In the metal paste according to the present inventors, a core/shell structure obtained by combining ceramic particles with the external surface of a core particle including precious metal to cover the external surface with the ceramic particles is applied to the configuration of the conductive particles. With the conductive particle having the core/shell structure, ceramic particles are dispersed finely during the step of firing the metal paste, in order to suppress the increase in the size of the ceramic powder that increases the resistance. As a result, the fired electrode becomes closely packed and the resistance thereof is low.

RELATED ART DOCUMENT

Patent Document

Patent Document 1: JP 4834170 B1

SUMMARY OF THE INVENTION

Problems to be Solved by the Invention

An electrode formed by the metal paste using conductive particles having the core/shell structure described above exhibits desired characteristics and the effectiveness thereof is confirmed when the electrode is applied to a lead wire, a heater electrode, and the like. However, as a result of studies performed by the present inventors, the present inventors have found that this electrode does not exhibit a sufficient performance as a gas sensor electrode serving as a sensitive unit for various kinds of gas sensors. A gas sensor electrode is required to have an electrode activity according to a gas type to be measured in an inspection gas, but a conventional electrode formed by a metal paste is inferior in this electrode activity.

Therefore, the present invention provides an electrode having a sufficient electrode activity as a gas sensor electrode for various kinds of gas sensors. In addition, the present invention provides a method of manufacturing this gas sensor electrode and a metal paste suitable therefor.

Means for Solving the Problems

In order to extract problems associated with a conventional electrode formed by a metal paste including conductive particles having the core/shell structure, first, the present inventors have reconsidered the structure of the gas sensor electrode. FIG. 1 illustrates a configuration of an oxygen sensor serving as an example of a general gas sensor. In FIG. 1, in a sensitive unit of the gas sensor, anode and cathode gas sensor electrodes are configured to sandwich a solid electrolyte. In the gas analysis using the gas sensor, a measurement gas (oxygen) introduced into the cathode electrode passes through the inside of the electrode and reaches the solid electrolyte. At this occasion, oxygen molecules are ionized due to the effect of the conductive metal particle phase (platinum and the like) in the cathode electrode, and pass through the solid electrolyte, so that the oxygen concentration is detected based on the change in the electric current caused thereby. In this measurement process, the reaction for the oxygen molecule detection occurs at a three-phase boundary shared by the conductive metal, the solid electrolyte, and the measurement gas (FIG. 2).

The present inventors considered that the conventional electrode formed by the metal paste having the core/shell structure is closely packed, but this closely packed state conversely causes a problem for the gas sensor electrode, and the three-phase boundary is not sufficiently formed in the electrode, and therefore, the electrode activity could not be obtained.

In order to sufficiently form the three-phase boundary in the electrode, the structure of the electrode is preferably porous, so that the reaction field of the gas is increased. However, use of a porous electrode is not enough. The gas sensor electrode is required to have an electrode activity for the measurement gas, but primarily, an electrical conductivity is required as the conductive member. With regard to this feature, in order to simply produce a porous electrode, for example, it is possible to apply a metal paste obtained by mixing conventional conductive particles and ceramic powder in which the diameters of the conductive particles are increased. In this case, however, the conductivity of the electrode is insufficient. This is because, in the metal paste in which the diameters of the conductive particles are simply increased, the fired conductive metal becomes excessively coarse, making it difficult for them to be close to each other, and the conductivity is not provided unless the electrode is made into a thick film. When the electrode is made into a thick film, the size of the sensor device increases, and in addition, the amount of use of metal (precious metal such as platinum) increases, which is disadvantageous in terms of the cost.

Therefore, the present inventors assume that the structure suitable for the gas sensor electrode is porous for forming many three-phase boundaries, and at the same time, a structure in which ceramic particles and conductive metal are highly dispersed with appropriate fineness for ensuring conductivity, and have conceived of the present invention clarifying such an electrode structure.

Accordingly, the present invention is directed to a sensor electrode including a conductive particle phase made of Pt or Pt alloy and a ceramic particle phase being mixed and dispersed, wherein a rate of content of the ceramic particle phase is 6.0 to 22.0 mass %, and a void ratio is 2.5 to 10.0%, and a dispersion degree of the conductive particle phase per length of 25 μm on the electrode surface is 0.60 to 0.85 μm, and a dispersion degree of the conductive particle phase in the electrode cross section per length of 100 μm in a direction parallel to the electrode surface is 2.0 to 4.0 μm.

In the sensor electrode according to the present invention, a void ratio in an electrode having a predetermined amount of ceramic particles mixed therein clearly indicates a preferred range of three-phase boundaries serving as the reaction field of gas. At the same time, dispersion degrees of the conductive particle phases on both of the surface and the cross section of the electrode are clearly indicated in order to define a preferred dispersion state of conductive particles.

The void ratio is a ratio of an area, in the cross section of the electrode, occupied by neither conductive particle phase nor ceramic particle in the electrode. When the void ratio is less than 2.5%, the electrode becomes too dense, and the reaction field for the gas becomes insufficient, which degrades the electrode activity. On the other hand, when the void ratio is more than 10.0%, the resistance of the electrode tends to be high.

In the present invention, the dispersion degrees of the conductive particle phases on the surface and the cross section of the electrode mean an average length for which the conductive particle phase exists with respect to a reference length in each surface. A method for measuring this dispersion degree includes, for example, applying image processing on structure photographs of the surface and the cross section of the electrode, drawing multiple reference lines, measuring and calculating the length of the conductive particle phase crossing each reference line, deriving an average value thereof, and adopting a result as a dispersion degree. Since the dispersion degree according to the present invention is related to the size of the conductive particle phase, the value thereof is preferably equal to or less than a predetermined value. More specifically, on the electrode surface, the dispersion degree is to be 0.85 μm or less per length of 25 μm, and in the electrode cross section, the dispersion degree is to be 4.0 μm or less per length of 100 μm in a direction parallel to the electrode surface. When the values are larger than the above, dispersion state tends to be such that the conductive particles are coarse and deviated, which may increase the resistance and decrease the electrode activity. The measurement direction of the reference length (25 μm) of the electrode surface may be either the longitudinal or lateral direction, but both are preferably adopted as references to obtain a predetermined dispersion degree.

The conductive particle phase includes Pt or Pt alloy. These metals are highly conductive and advantageous in heat resistance property and corrosion resistance property. Some of various kinds of sensors are used at a high temperature such as an exhaust sensor of a vehicle, and therefore, these metals are preferable as electrode materials for such sensors. Which of Pt and Pt alloy is used as the conductive particle may be selected in accordance with the purpose and the required characteristics. Pt has a lower resistance than Pt alloy, and is preferable for an electrode that is required to have a lower resistance. On the other hand, Pt alloy has a higher resistance than Pt but has a lower temperature coefficient of resistance (TCR), and therefore, Pt alloy is preferable for an electrode that is required to have a lower TCR.

When Pt alloy is applied, a metal to make an alloy with Pt is preferably Pd, Au, Ag, or Rh. Pt—Pd alloy including Pd is well suited to ceramics which serves as a substrate, and is preferable since it has a high degree of wettability when made into paste. Note that Pt—Pd alloy preferably has a Pd content of 30 mass % or less. This is because, when the Pd content is too high, Pd oxide is likely to be deposited in the firing step, which reduces the reliability of the electrode.

The ceramic preferably includes a ceramic including $ZrO_2$. A ceramic mixed in a conventional metal paste is to be applied in view of a shrinkage rate adjustment effect for a substrate, which is an original function of the ceramic. Examples of ceramics including $ZrO_2$ include not only pure zirconia but also stabilized zirconia to which several % of oxide such as yttria and calcia is added. In addition, $ZrO_2$ mixed with other oxides such as $Al_2O_3$ can also be applied. Note that, basically, this ceramic phase is preferably of the same material as the ceramic used for the substrate, and therefore, the ceramic phase may include ceramics (oxides such as La, Ce, Pr, Nd, Sm, and Hf) having oxide ion conductivity other than $ZrO_2$.

In the gas sensor electrode according to the present invention, the content of the ceramic phase is 6.0 to 22.0 mass %. When the ceramic phase is little, the conductive particle phase tends to be coarse and the dispersion state tends to be deviated. When the ceramic phase is too much, on the other hand, the resistance becomes too high, which may make it impossible for the electrode to act as an electrode.

A method of manufacturing the gas sensor electrode according to the present invention includes firing a metal paste, which is basically the same as a conventional technique. However, the conventional metal paste is not applicable in order to produce an electrode having an appropriate void ratio while having fine conductive particles dispersed therein as described above.

Therefore, the present inventors have used the effect of the conductive particles having the core/shell structure developed by the present inventors. More specifically, the present inventors have used the feature of making the conductive metal and the ceramic phase into a preferable state even after firing. Then, the present inventors have found that a porous and highly dispersed electrode film can be formed by adjusting the particle diameters of the conductive particles having the core/shell structure while suppressing formation of coarse particles, and mixing ceramic particles having appropriate particle diameters into the metal paste. As a result, the present inventors conceived of a metal paste for forming a sensor electrode according to the present invention.

A metal paste for forming a sensor electrode according to the present invention is a metal paste for forming a sensor electrode, in which a conductive particle having a core/shell structure including a core particle made of Pt or Pt alloy and a shell made of ceramic covering at least a portion of the core particle and ceramic powder are dispersed in a solvent, wherein the conductive particle is a particle of which average particle diameter is 90 to 500 nm, and the core particle is covered with ceramic of 0.5 to 3.0 mass % with respect to the mass of the conductive particle, a content of the ceramic powder is 5 to 20 mass % with respect to a total mass of the conductive particle and the ceramic powder, a total content of a ceramic component in a metal paste is 6.0 to 22.0 mass % with respect to the total mass of the conductive particle and the ceramic powder, and further, a dispersion degree measured according to a line transect method based on a grind gauge is equal to or less than 15 μm.

Hereinafter, this metal paste for forming a gas sensor electrode will be described in detail. As described above, the metal paste according to the present invention is made by dissolving, into a solvent, the conductive particles having the core/shell structure adjusted to have a predetermined particle diameter and ceramic powder dispersed separately from the conductive particles.

The reason why the conductive particles having the core/shell structure are used in the present invention is to utilize this basic effect of the conventional art found by the present inventors. More specifically, in the step of firing paste including the conductive particles having the core/shell structure, first, the shell (ceramic) is released from the core particle, and thereafter the core particle is sintered. The temperature of this ceramic release is higher than the sintering temperature of the core particle in the metal state. While the conductive metal is covered with the shell, the conductive metal cannot be sintered. When the shell is released, the conductive metal starts to be sintered. At this stage, the ceramic which used to be the shell also starts to be sintered, and therefore, both of the particles are sintered uniformly without being made coarse, and a preferable dispersion state can be maintained.

The reason why ceramic powder is separately added in addition to the conductive particles in the present invention is because this ceramic powder serves as a frame for a porous electrode after the metal paste is fired, whereby the porosity of the electrode is ensured. The mechanism for achieving this effect will be hereinafter described. The sintering of the conductive particles having the above core/shell structure is realized at a time relatively earlier than the sintering of the ceramic powder separately added. That is, the ceramic which becomes the shell is a so-called protective film that suppresses the sintering of the core particle as described above, but when the amount of ceramic is less, the temperature thereof becomes closer to the sintering temperature of the core particle itself, and shifts to a lower temperature side. Therefore, by appropriately setting the bonding amount of ceramic which becomes the shell, the conductive particles can be sintered before the separately added ceramic powder is sintered. Then, the ceramic and the conductive metal derived from the conductive particles are sintered in a fine state, and the ceramic powder separately added is thereafter sintered, whereby an electrode having a desired structure can be made. As described above, according to the present invention, the sintering of the conductive particles and the sintering of the ceramic powder are done at different points in time in order to delay the sintering of the ceramic powder serving as the frame, and the porosity is ensured by preventing the entire electrode from being sintered at a time and avoiding the closely packed state.

As described above, the sintering of the conductive particles having the core/shell structure and the sintering of the separately added ceramic powder are done at different points in time, so that the conductive metal phase and the ceramic phase are partially in a fine and high dispersion state, but still can be made into a porous state as a whole. In this case, the timing of the sintering of the conductive particles having the core/shell structure differs in accordance with the particle diameters thereof, and further, in accordance with the bonding amount of the ceramic, and therefore, the ranges thereof are important factors.

The average particle diameter of the conductive particles according to the present invention is 90 to 500 nm. This is relatively coarse with respect to the conductive particles having the core/shell structure found by the present inventors described above. The reason why the average particle diameter is defined in the above range is to set the sintering temperature of the conductive particle in an appropriate range. More specifically, the sintering of the metal paste occurs at a lower temperature as the particle diameters of the conductive particles are smaller. Therefore, when the average particle diameter of the conductive particles is too small, the sintering of the conductive particles is completed in a very earlier stage than the sintering of the separately added ceramic powder, and the conductive particles may ultimately become coarse. On the other hand, the upper limit value of the average particle diameter of the conductive particles is required in order to produce a highly dispersed electrode. As described above, the average particle diameter of the conductive particles is set from the perspective of the adjustment of sintering timing and in view of the effect of the ceramic which becomes the shell.

Another significance of setting the average particle diameter of the conductive particles is to adjust the shrinkage rate of the metal paste during sintering to be closer to that of the substrate (green sheet). In the invention of the present application in which the ceramic powder is mixed separately from the conductive particles, it is necessary to set the sintering temperature in view of not only the sintering of the conductive particles but also the sintering of the separately added ceramic powder. When the particle diameter of the conductive particles is too small, the difference increases between the sintering temperature of the conductive particles (low temperature side) and the sintering temperature of the ceramic powder (high temperature side), and in a case where firing is performed at a high temperature side in order to sinter the entire conductive particles and ceramic powder, the shrinkage rate becomes excessively high, and the substrate may deform and the electrode film may break. Therefore, the conductive particles are made to be somewhat coarse, and the sintering temperature thereof is adjusted, so that the sintering temperature of the entire metal paste is made to be uniform.

In the conductive particles having the core/shell structure, the bonding amount of the ceramic which becomes the shell is 0.5 to 3.0 mass % which is determined based on the mass of the entire conductive particles. When the bonding amount of the ceramic is less than 0.5 mass %, the heat resistance property of the conductive particle is insufficient, and the timing of the sintering is not adjusted as described above, so that the sintering of the conductive metal occurs earlier to enhance coarse property. When the ceramic of more than 3.0 mass % is bonded, on the other hand, the heat resistance property becomes too high, which delays the timing of the sintering. As a result, the sintering occurs at the same time as the sintering of the separately added ceramic powder, which makes the electrode more closely packed.

The reason why ceramic powder is added in addition to the conductive particles in the metal paste according to the present invention is because this ceramic powder serves as a frame for forming a porous electrode as described above. In addition, the separately added ceramic powder also has the effect of suppressing locally making the conductive particles coarser in the step of adjusting the particle diameter of the conductive particles having the core/shell structure in the production of the metal paste according to the present invention. This feature will be described later.

In this case, the addition amount of the separately added ceramic powder is 5 to 20 mass % with respect to the total mass of the ceramic powder and the conductive particles in the metal paste. When the addition amount is less than 5 mass %, this is insufficient as the frame for obtaining the porous structure of the electrode, which makes the electrode more closely packed. When the addition amount is more than 20 mass %, it is difficult to obtain a proximity state of the conductive metal in the electrode, and this may reduce the conductivity and lose the function of the electrode. A more preferable range of the addition amount of the ceramic powder is 5 to 15 mass %. The particle diameter of the ceramic powder is preferably 100 to 500 nm. This is because the coarse ceramic powder reduces the dispersion of the conductive particles in the electrode. In addition, since the ceramic powder acts as the frame of the electrode, excessively fine ceramic powder affects the porosity of the electrode.

The ceramic component, derived from the ceramic which becomes the shells of the conductive particles, and the separately added ceramic powder forms the ceramic particle phase of the electrode. Therefore, the total content of the ceramic component in the metal paste is 6.0 to 22.0 mass % with respect to the solid portion of the metal paste (the total mass of the conductive particles and the ceramic powder). Therefore, when the amount of covering of the ceramic which becomes the shell of the conductive particle is small (around 0.5 mass % which is the lower limit value thereof), it is necessary to adjust the amount of mixed ceramic, so that the ceramic component stays within the range described above.

In the metal paste according to the present invention, the particle diameter of the conductive particles is adjusted to be in an appropriate range, but in addition to this, it is necessary to prevent coarse particles from being mixed. The coarse particles have particle diameters several to several dozen times larger than the average particle diameter of the conductive particles. The coarse particles are likely to be generated during thermal treatment for particle diameter adjustment of the conductive particles described later. When the metal paste having such coarse particles generated and mixed therein is made into a gas sensor electrode, such coarse particles exist as they are, and form an area where a measurement substance such as oxygen cannot enter, and the activity with respect to the amount of used platinum tends to decrease. The metal paste including coarse particles has a lower degree of printability, and may leave a line-like mark on a surface to which the paste has been applied.

Therefore, in the metal paste according to the present invention, the dispersion degree measured according to a line transect method using a grind gauge is 15 µm or less. The grind gauge is an apparatus for measuring and evaluating the dispersion property of particles included in paste, ink, and the like. In the present invention, the dispersion degree measured according to the line transect method using the grind gauge, i.e., the numeric value at the position where the third line (line-like mark) is generated needs to be 15 µm or less. Note that the value of the dispersion degree of the metal paste defined by the grind gauge can be made zero by setting the particle diameter of dispersion particles in the paste to a smaller particle diameter and completely eliminating coarse particles, but when the productivity is considered, 1 µm is preferably adopted as the lower limit.

Note that the conductive particle includes Pt or Pt alloy. The Pt alloy is preferably Pt—Pd alloy in which the Pd content is 30 mass % or less. The ceramic and the separately added ceramic powder added as the shell to the outer periphery of the conductive particles are preferably ceramic including $ZrO_2$, and the range thereof is the same as what has been described above.

The metal paste according to the present invention is made by dispersing the conductive particles and the ceramic powder into a solvent. Examples of solvents applicable to metal paste production in the present invention include general solvents such as ethylene glycol, propylene glycol, ethyl cellosolve, butyl cellosolve, ethylene glycol monophenyl ether, ethylene glycol monomethyl ether acetate, benzyl alcohol, kerosene, paraffin, toluene, cyclohexanone, γ-butyrolactone, methyl ethyl ketone, N-methyl pyrrolidone, N-dimethylformamide, N-methylacetamide, N,N-dimethylacetamide, butyl carbitol, turpentine oil, α-terpineol, and terpineol. More specifically, α-terpineol or the like is preferable.

The mixing amount of the conductive particles and the ceramic powder in the metal paste is preferably such that the mixed powder thereof is 50 to 90 mass % with respect to the entire paste. This is because, when it is less than 50 mass %, the electrode film becomes too thin, and when it is more than 90 mass %, it is difficult to make paste.

In addition, generally-used resin may be added to give viscosity and thixotropy to the metal paste. Examples of such resins generally include natural resin, amino resin, and alkyd resin. More particularly, ethylcellulose or the like is preferred.

Next, a method of manufacturing metal paste according to the present application will be described. As described above, the metal paste according to the present invention can be produced by mixing the conductive particles having the core/shell structure and ceramic powder with the solvent. In this case, the method of manufacturing the conductive particles having the core/shell structure is also disclosed in Patent Document 1 described above, and an example thereof includes a method using gas phase reaction in a high temperature atmosphere. In this method, metal alloy powder which becomes core particles and ceramic powder which becomes shells are mixed, and this mixed powder is discharged into a high temperature atmosphere equal to or higher than boiling points of both of the components, whereby fine powder generated by cooling the mixed powder is collected.

Then, in the present invention, the composite particles having the core/shell structure are not made into conductive particles as they are, and it is necessary to adjust the particle diameters thereof. In the particle diameter adjustment of the composite particles, the particle diameters of the core particles can be increased by heat treatment (granulation treatment) (Patent Document 1). However, generation of excessively coarse conductive particles cannot be suppressed by just performing thermal treatment on the composite particles. This is because, in the particle diameter adjustment of the composite particles having the core/shell structure based on heat treatment, composite particles having thin shells tend to be bonded with each other to make coarse state, and therefore, when heat treatment is simply performed, composite particles are locally bonded to make coarse state. The existence of the coarse particles results in reduction of the activity when an electrode is made, and in addition, the printing property of the metal paste is deteriorated, which are therefore not preferable as described above.

The present inventors have decided to mix and disperse the ceramic powder into the composite particles having the core/shell structure and thereafter perform heat treatment in order to suppress local generation of coarse particles while the particle diameter adjustment of the composite particles is still performed. As described above, the ceramic powder is mixed and dispersed into the composite particles, so that the ceramic powder acts as a barrier for blocking the movement and sintering of the composite particles, whereby excessive bonding of the composite particles can be suppressed.

In heat treatment of the composite particles according to the present invention, it is necessary to mix and disperse the ceramic powder into the composite particles before the heating. The average particle diameter of the composite particles mixed here is preferably 10 to 25 nm, and on the other hand, the ceramic powder preferably has a particle diameter of 100 to 500 nm. The mixing amount of the ceramic powder is preferably the same as the mixing amount thereof in the metal paste which becomes the product. More specifically, it is preferably 5 to 20 mass % with respect to the total mass of the conductive particles and the ceramic powder. When the composite particles and the ceramic powder are mixed, it is preferable to uniformly mix them to disperse the ceramic powder. For this purpose, it is preferable to apply precise mixing means such as a ball mill, a jet mill, a bead mill, and a roll mill.

A heat treatment temperature is 700 to 1200° C. in heat treatment for particle diameter adjustment of the conductive particles. This is because, at a temperature lower than 700° C., the bonding of the composite particles is insufficient, and it is difficult to make an adjustment to attain a predetermined particle diameter, and on the contrary, when the temperature is higher than 1200° C., the composite particles become coarse. Note that the heating time of this thermal treatment is preferably 0.5 to 10 hours.

The mixed particles of the conductive particles and the ceramic powder having been subjected to heat treatment can be used as precursor of metal paste as they are, and when the mixed particles are dispersed into a solvent, they can be made into metal paste for forming an electrode.

When the electrode is produced using the metal paste, the firing temperature is preferably 1300 to 1600° C. This is because the electrode with a low resistance value can be obtained by sufficiently performing a sintering process. In the electrode film thus formed, fine ceramic particles are dispersed.

Advantageous Effects of the Invention

As described above, the sensor electrode according to the present invention has the porous structure appropriately including the three-phase boundaries required as reaction fields, and appropriately fine conductive particles and ceramic particles are dispersed therein, so that the resistance value is low while the activity is high. In addition, the metal paste according to the present invention can form such a preferable electrode, and the electrode film can be made thin. This reduces the amount of use of precious metals such as Pt and the cost of electronic devices.

DESCRIPTION OF EMBODIMENTS

First Embodiment

Figure 1:
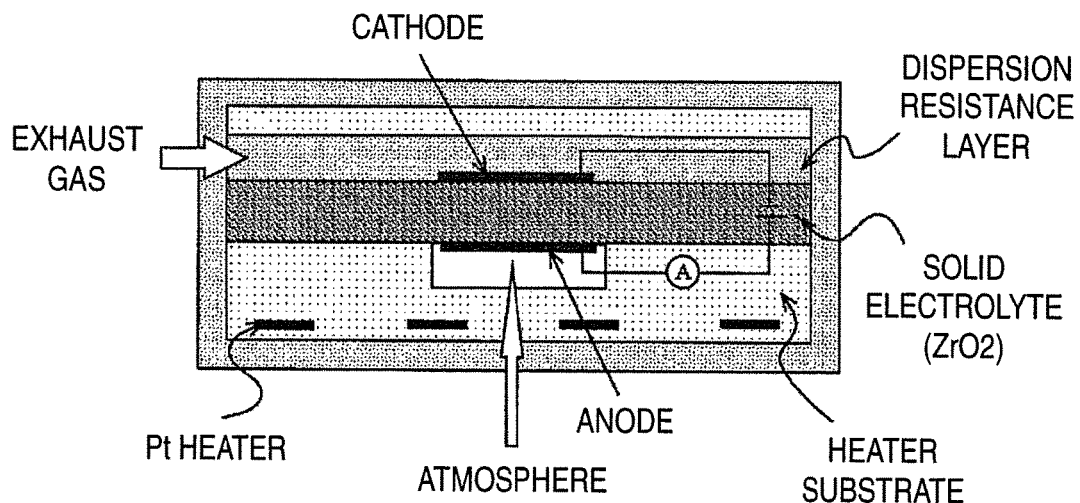
FIG. 1 is a diagram for illustrating a structure of a general oxygen sensor.
Figure 2:
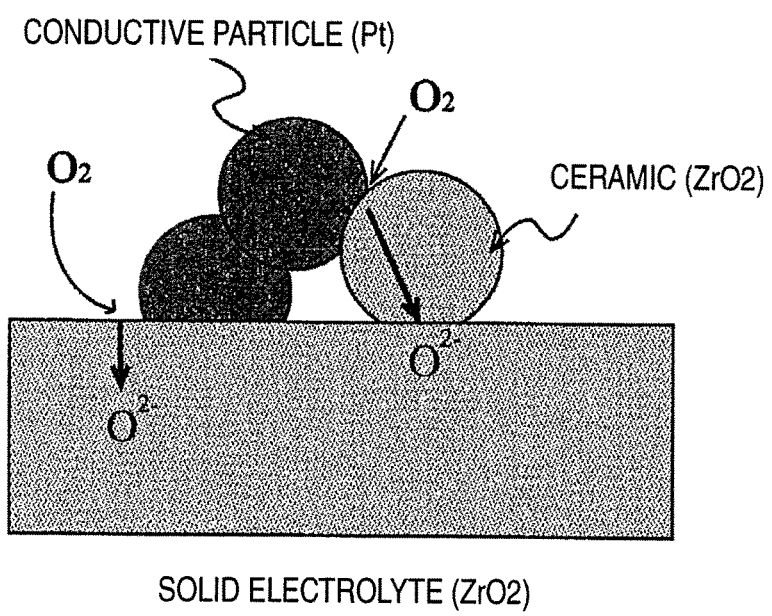
FIG. 2 is a diagram for illustrating the details of the inside of an electrode of the oxygen sensor (three-phase boundary).

Hereinafter, an embodiment of the present invention will be described. In the present embodiment, Pt is adopted as core particles, composite particles bonded with $ZrO_2$ (yttria stabilized zirconia) were prepared as ceramic which becomes shells, $ZrO_2$ (yttria stabilized zirconia) was added thereto as ceramic powder, and thermal treatment was performed to adjust particle diameter. Then, a metal paste was produced, and an electrode made by firing the metal paste was subjected to characteristics evaluation.

To make composite particles having the core/shell structure, Pt fine powder having an average particle diameter of 10 nm and $ZrO_2$ powder (yttria stabilized zirconia) having an average particle diameter of 10 nm are uniformly mixed by a V-type mixing machine, and this mixed powder was discharged into a plasma atmosphere under an argon atmosphere by means of a high frequency induction heating plasma apparatus. Then, the generated fine powder was collected by a filter. Through this step, composite particle powder having the core/shell structure, in which Pt is adopted as core particles and $ZrO_2$ is adopted as shells, was obtained. In this case, the composite particle powder was prepared in which the mixing amount of the ceramic with respect to the entire mixed powder was adjusted, and the bonding amount of the ceramic which becomes the shell was changed. In the present embodiment, composite particles having ceramic amounts of 0.5 wt % (Example 1, Comparative Example 1), 1.0 wt % (Examples 2, 3), 1.6 wt % (Examples 4, 5), 3.0 wt % (Examples 6, 7), and 6.1 wt % (Comparative Examples 2, 3) were prepared.

Subsequently, thermal treatment for particle diameter adjustment of the conductive particles was performed. First, $ZrO_2$ powder having the same composition as the shell was added to the composite particles, and was mixed sufficiently by a planetary mill. Then, after the mixed powder was dried, heating is performed at 800° C. for one hour, and particle diameter adjustment is performed. The amounts of mixing of the $ZrO_2$ powder with respect to the mixed powder are 5 wt % and 10 wt %.

Then, a metal paste was produced from each mixed powder. In the production of the metal paste, the mixed powder having been subjected to thermal treatment was put into ester alcohol which is an organic solvent, and further, a diamine-based surfactant and ethylcellulose were mixed therewith and, using a triple roll mill, they were mixed and kneaded to be made into paste. The mixing amount of the mixed powder with respect to the entire paste was 80 mass %.

Conventional Example 1

Conductive particles (ceramic amount 1.6 wt % which is a shell) of Examples 4, 5 are prepared as conventional conductive particles having the core/shell structure. Then, thermal treatment is applied to the conductive particles without mixing any ceramic powder, and the thermally treated conductive particles and ceramic powder are mixed (10 wt % with respect to the entire mixed powder). Then, the mixed powder was made into a metal paste.

Conventional Example 2

As a conventional metal paste including conductive particles not having the core shell structure, a metal paste obtained by separately mixing Pt powder and ceramic powder was produced. Pt powder having a particle diameter of 5 μm was used as Pt powder, and $ZrO_2$ powder (11.4 wt %) was used as ceramic powder, so that powder for a metal paste was made, which was in turn made into a metal paste.

In Examples 1 to 7, Comparative Examples 1 to 3, and Conventional Examples 1 to 2, the particle diameters of the composite particles (conductive particles) in the steps from the production of the composite particles to the particle diameter adjustment in the powder state before made into a paste were converted from specific surface area measurement based on a BET three-points method. In the dispersion property evaluation of the particles, the dispersion degrees are measured according to the line transect method using a grind gauge. In the dispersion degree measurement, a grind gauge (maximum scale 25 μm) manufactured by Tsutsui Scientific Instruments Co., Ltd. was used, a paste was dropped to the maximum groove depth portion of the gauge, line-like marks appearing on a paste coating film obtained by scraping the paste with a scraper were observed, and the depth (μm) of the groove at a point where the third line appears was measured. This was performed three times, and the average thereof was evaluated as the dispersion degree. These values are shown in Table 1.

In Table 1, it is understood from the results of Examples, Comparative Examples, and Conventional Example 1 that the conductive particles having the core/shell structure have larger particle diameters due to thermal treatment. However, it is understood that, when the ceramic powder is not mixed before thermal treatment like Conventional Examples, the particle diameter of the conductive particles does not become excessively large, but the dispersion degree increases after the paste is produced. This is because, when the ceramic powder does not exist during thermal treatment, coarse particles are generated locally, and it can be said that the coarse particles exist without collapsing even by the mixing during the production of the paste. These facts indicate that, by mixing the ceramic powder before thermal treatment, the generation of the coarse particles is suppressed, and it is possible to obtain powder having uniform particle diameters.

Subsequently, an electrode was formed from the produced metal paste, and evaluation thereof was performed. The electrode was formed by applying the metal paste onto a 99 mass % zirconia green sheet by screen printing. Thereafter, the electrode was dried at 80° C. for 20 minutes, and firing treatment was performed at 1450° C. for one hour, so that an electrode film was produced. Two types of electrodes were produced, which have φ7.8 mm and thicknesses of 3 μm and 7 μm, respectively.

Structure observation was performed on each electrode film produced, and the structure thereof (the void ratio, the dispersion degree of the conductive particles on the surface and in the cross section) was measured. This measurement is based on image analysis of a structure photograph on the surface and in the cross section of each electrode. To measure the void ratio, the area of a black point in the picture is derived as a void portion, and the ratio of the area is derived based on the area of the observation. To measure the dispersion degree in the electrode cross section, a measurement region of 5 μm×100 μm is extracted from the cross-sectional organization, and in this measurement region, five reference lines (lines of a length 100 μm with an interval of

TABLE 1

| | The amount of ceramic | | | Particle diameter | | | | Grind gauge |
| | | | | Conductive particle | | Ceramic powder | | |
| | Shell | Separately added | Total amount | Before thermal treatment | After thermal treatment | Before thermal treatment | After thermal treatment | dispersion degree |
|---|---|---|---|---|---|---|---|---|
| Example 1 | 0.5 wt % | 10 wt % | 10.5 wt % | 18.1 nm | 480 nm | 169.3 nm | 169.8 nm | 8.8 μm |
| Example 2 | 1.0 wt % | 5 wt % | 6.0 wt % | 18.1 nm | 481 nm | 169.1 nm | 169.9 nm | 12.5 μm |
| Example 3 | | 10 wt % | 10.9 wt % | 18.1 nm | 327 nm | 169.4 nm | 169.7 nm | 9.2 μm |
| Example 4 | 1.6 wt % | 5 wt % | 6.5 wt % | 18.8 nm | 140 nm | 169.1 nm | 169.9 nm | 12.7 μm |
| Example 5 | | 10 wt % | 11.4 wt % | 18.8 nm | 102 nm | 169.5 nm | 169.3 nm | 7.8 μm |
| Example 6 | 3.0 wt % | 5 wt % | 7.9 wt % | 19.3 nm | 155 nm | 169.9 nm | 169.2 nm | 7.2 μm |
| Example 7 | | 10 wt % | 12.8 wt % | 19.3 nm | 101 nm | 169.2 nm | 169.3 nm | 7.5 μm |
| Comparative Example 1 | 0.5 wt % | 5 wt % | 5.5 wt % | 18.1 nm | 889 nm | 169.6 nm | 169.8 nm | 13.3 μm |
| Comparative Example 2 | 6.1 wt % | 5 wt % | 10.8 wt % | 27.1 nm | 82 nm | 169.6 nm | 169.2 nm | 7.2 μm |
| Comparative Example 3 | | 10 wt % | 15.5 wt % | 27.1 nm | 77 nm | 169.3 nm | 169.6 nm | 6.5 μm |
| Conventional Example 1 | 1.6 wt % | 10 wt %* | 11.4 wt % | 18.1 nm | 144 nm | 169.5 nm | — | 17.5 μm |
| Conventional Example 2 | — | 11.4 wt % | 11.4 wt % | 5 μm | — | 169.5 nm | — | 11.2 μm |

*Ceramic powder is added after thermal treatment of conductive particles.

1 μm) are drawn, the number of dots of the conductive particle phase thereon is measured for each reference line, and the average value thereof was measured. To measure the dispersion degree on the electrode surface, a measurement region of 25 μm×25 μm was extracted from the surface structure, six reference lines (lines of a length 25 μm with an interval of about 4 μm) are drawn, and likewise, the number of dots of the conductive particle phase and the average thereof were measured.

In order to evaluate the electrode activity (electric conductivity) of each electrode, the electrode resistance relative to the platinum weight per unit area is measured according to an alternate current impedance method. As the evaluation condition, under 800° C. atmosphere, the frequency response of an electric current to a voltage of a frequency from 100 kHz to 30 mHz with an amplitude of 20 mV without DC bias was measured. Then, a measurement result of a film thickness of 7 μm according to Conventional Example 2 was adopted as the reference value, those having substantially equivalent characteristics to the reference value were evaluated as "Δ", those having better characteristics than the reference were evaluated as "○", and those having extremely better characteristics than the reference value were evaluated as "⊙". Those that cannot be measured because of excessively high resistances of the electrode were evaluated as "x". Table 2 shows results of characteristics evaluations.

conductive particles not having the core/shell structure and the ceramic powder can produce an electrode having a porous structure, but the conductive particles are coarse and the resistance value is high, making the metal paste (Conventional Example 2) inferior in conductivity. For this reason, it is difficult for the metal paste to act as an electrode using a thin film.

However, even with the conductive particles having the core/shell structure, when the amount of ceramic which becomes the shells is small, the conductive particles become coarse and, when the ceramic amount is large, it is difficult to obtain a porous electrode (Comparative Examples 1 to 3). As described above, this is considered to be because, when the ceramic is little, the sintering of the conductive particles advances too quickly, and when the ceramic is too much, the timing of the sintering of the conductive particles is out of the expected timing, and it occurs at the same point in time as the sintering of the mixed ceramic powder.

Figure 3:
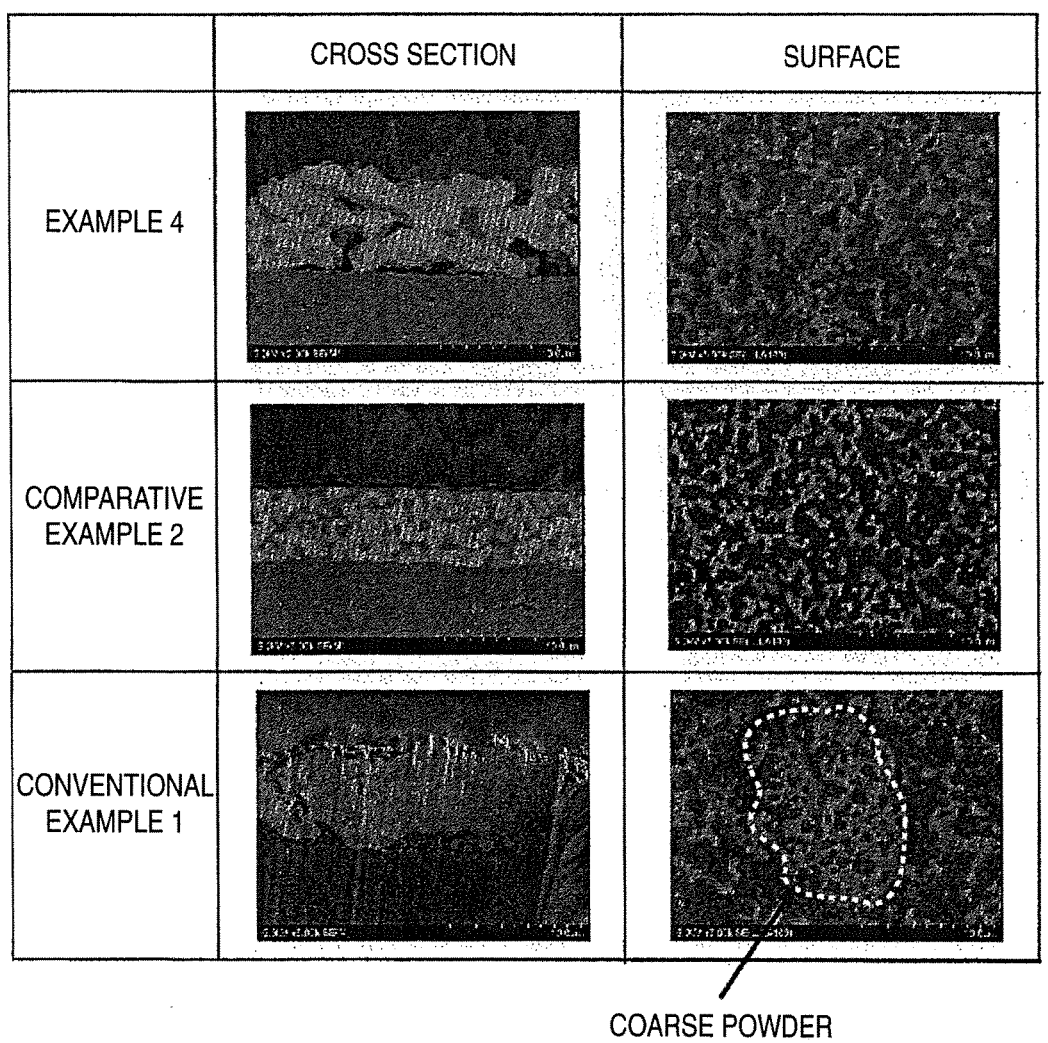
FIG. 3 is cross-sectional pictures and surface pictures of electrode films according to Example 4, Comparative Example 2, and Conventional Example 1.

With regard to produced electrodes, structure photographs (cross section, surface) of Example 4, Comparative Example 2, and Conventional Example 1 are shown in FIG. 3. In Conventional Example 1, the coarse powder generated when the conductive particles were thermally treated remained on the electrode. As compared with Example 4, it is understood that the closely packed film with little voids included therein was made according to Comparative Example 2.

TABLE 2

| | The amount of ceramic | | | Electrode structure | | | Characteristics evaluation | |
| | | | | | Dispersion degree(μm) | | | |
| | Shell | Separately added | Total amount | Void ratio(%) | Cross section | Surface | 3 um | 7 um |
|---|---|---|---|---|---|---|---|---|
| Example 1 | 0.5 wt % | 10 wt % | 10.5 wt % | 4.49 | 3.1 | 0.73 | ⊙ | ⊙ |
| Example 2 | 1.0 wt % | 5 wt % | 6.0 wt % | 9.53 | 3.8 | 0.84 | ○ | ○ |
| Example 3 | | 10 wt % | 10.9 wt % | 8.49 | 3.0 | 0.60 | ⊙ | ⊙ |
| Example 4 | 1.6 wt % | 5 wt % | 6.5 wt % | 6.76 | 3.9 | 0.60 | ○ | ○ |
| Example 5 | | 10 wt % | 11.4 wt % | 4.59 | 3.3 | 0.65 | ⊙ | ⊙ |
| Example 6 | 3.0 wt % | 5 wt % | 7.9 wt % | 2.75 | 3.8 | 0.74 | ○ | ○ |
| Example 7 | | 10 wt % | 12.8 wt % | 6.49 | 2.0 | 0.73 | ⊙ | ⊙ |
| Comparative Example 1 | 0.5 wt % | 5 wt % | 5.5 wt % | 4.56 | 5.6 | 0.86 | Δ | Δ |
| Comparative Example 2 | 6.1 wt % | 5 wt % | 10.8 wt % | 0.11 | 2.3 | 0.54 | Δ | X |
| Comparative Example 3 | | 10 wt % | 15.5 wt % | 0.19 | 2.0 | 0.80 | Δ | X |
| Conventional Example 1 | 1.6 wt % | 10 wt %* | 11.4 wt % | 5.12 | 4.7 | 0.98 | Δ | Δ |
| Conventional Example 2 | — | 11.4 wt % | 11.4 wt % | 14.66 | 5.0 | 1.02 | X | Δ |

*Ceramic powder is added after thermal treatment of conductive particles.

As can be understood from Table 2, the electrode films (Examples 1 to 7) made of metal pastes including the conductive particles having the core/shell structure of which particle diameters are appropriately adjusted and mixed with ceramic powder have a porous structure but still have relatively fine conductive metal dispersed therein. In contrast, the metal paste (Conventional Example 1) obtained by performing thermal treatment with only the conductive particles having the core/shell structure and mixed with ceramic after thermal treatment includes coarse particles, and therefore the dispersion degree of the platinum particles is out of a preferred range, and the metal paste (Conventional Example 1) is inferior in conductivity. The metal paste (Conventional Example 2) made by simply mixing the Second Embodiment In this case, the effect of the addition amount of ceramic powder mixed with the conductive particles has been considered. In addition to the electrodes produced according to the first embodiment (Examples 4, 5 and Conventional Example 2), electrodes were produced by means of metal pastes where the amounts of addition of ZrO$_2$ powder mixed with the conductive particles having the core/shell structure (ceramic amount: 1.6 wt %) are 15 wt % (Example 8), 20 wt % (Example 9), 1 wt % (Comparative Example 4), 3 wt % (Comparative Example 5), and 25 wt % (Comparative Example 6), and the resistance values and the electrode activity thereof were measured.

In the evaluation of the resistance values, the sheet resistance values per platinum weight in the electrode were evaluated. The sheet resistance value was measured by printing and firing an evaluation paste on a zirconia green sheet, making a line of 4 mm×16 mm (film thickness: 3 μm), and measuring the resistance values at both ends thereof by means of a digital multi-meter.

In order to evaluate the electrode activity (electric conductivity) of each electrode, the electrode resistance relative to the platinum weight per unit area was measured according to an alternate impedance method. As the evaluation condition, the evaluation paste was printed and fired on both surfaces of the zirconia green sheet, an electrode which has φ7.8 mm and a thickness of 3 μm was made, and under 800° C. atmosphere, the frequency response of an electric current to a voltage of a frequency from 100 kHz to 30 mHz with an amplitude of 20 mV without DC bias was measured.

Figure 4:
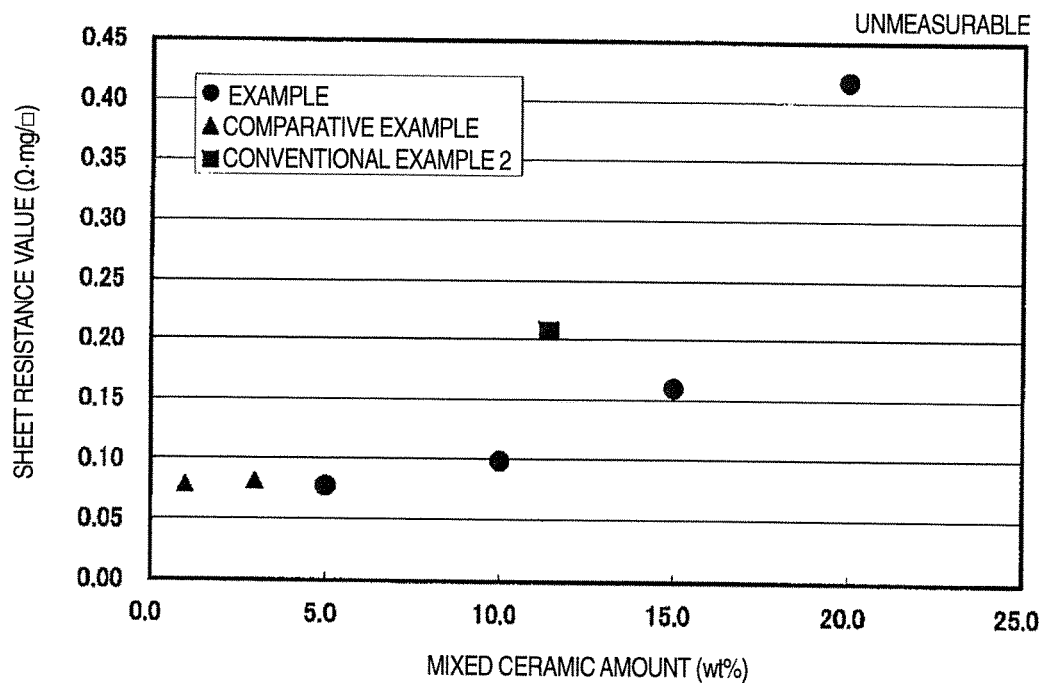
FIG. 4 is a measurement result of electrode resistances with respect to a platinum weight per unit area of electrode films formed by means of various kinds of metal pastes.
Figure 5:
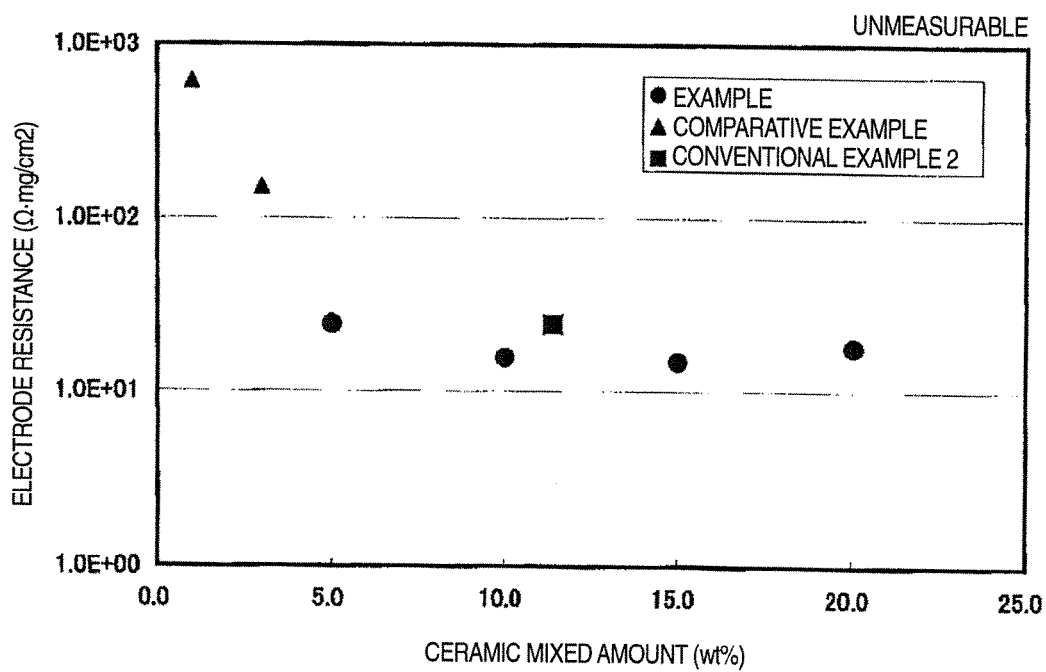
FIG. 5 is a measurement result of electrode activity of electrode films formed using various kinds of metal pastes.

These evaluation results are shown in Table 3 and FIGS. 4 and 5. Note that these evaluation results indicate the same examination result obtained in association with the electrode (film thickness: 7 μm) formed by the paste according to Conventional Example 2.

tive Example lies in the difference in the structure between the electrode films, and it is understood that the gas sensor electrode is preferably porous.

Considering both of the measurement results of the resistance value and the electrode activity, it is understood that the mixing amount of the ceramic needs to be 5 to 20 mass % in order to obtain a practical electrode that exhibits the electrode activity and still has a low sheet resistance. The electrode thus produced exhibits better characteristics even with a thinner film than Conventional Example 2. If Conventional Example 2 is made to have a thin film, the electrode activity cannot be measured (see Table 2), and therefore, the measurement result of the thick film is taken into consideration. Because of this fact, the superiority of the paste according to the present invention can be confirmed.

Third Embodiment

In this case, the technical significance of the particle diameter adjustment of the conductive particles having the core/shell structure has been considered. As described above, the particle diameter adjustment of the conductive

TABLE 3

| | The amount of ceramic | | | Evaluation result* | |
|---|---|---|---|---|---|
| | Shell | Separately added | Total amount | Sheet resistance value Ω · mg/□ | Electrode resistance Ω · mg/cm2 |
| Example 4 | 1.6 wt % | 5 wt % | 6.5 wt % | 0.0786 | 24.46 |
| Example 5 | | 10 wt % | 11.4 wt % | 0.0999 | 15.75 |
| Example 8 | | 15 wt % | 16.4 wt % | 0.1612 | 14.92 |
| Example 9 | | 20 wt % | 21.3 wt % | 0.4167 | 18.87 |
| Comparative Example 4 | 1.6 wt % | 1 wt % | 2.6 wt % | 0.0791 | 611.42 |
| Comparative Example 5 | | 3 wt % | 4.6 wt % | 0.0823 | 150.98 |
| Comparative Example 6 | | 25 wt % | 26.2 wt % | Unmeasurable | Unmeasurable |
| Conventional Example 2 | — | 11.4 wt % | 11.4 wt % | 0.2079 | 28.46 |

*Examples 4, 5, 8, 9 and Comparative Examples 4 to 6 are measurement values of film thickness 3 μm, and Conventional Example 2 is measurement value of film thickness 7 μm.

It is confirmed from Table 3 and FIG. 4 that the mixed ceramic amount affects the resistance value of the electrode. When the mixing amount of the ceramic is 5 mass % or less, the resistance value of the electrode is substantially constant and this can be said to be a low resistance. When the mixing amount of the ceramic exceeds 10 mass %, an increase in the mixing amount of the ceramic increases the resistance value, and the resistance is too high at 25 mass % (Comparative Example 6), making it impossible to perform the measurement. Even in a case of simply mixing the platinum powder and the ceramic powder according to Conventional Example 2, there would be basically no problem from the perspective of the resistance value.

Figure 6:
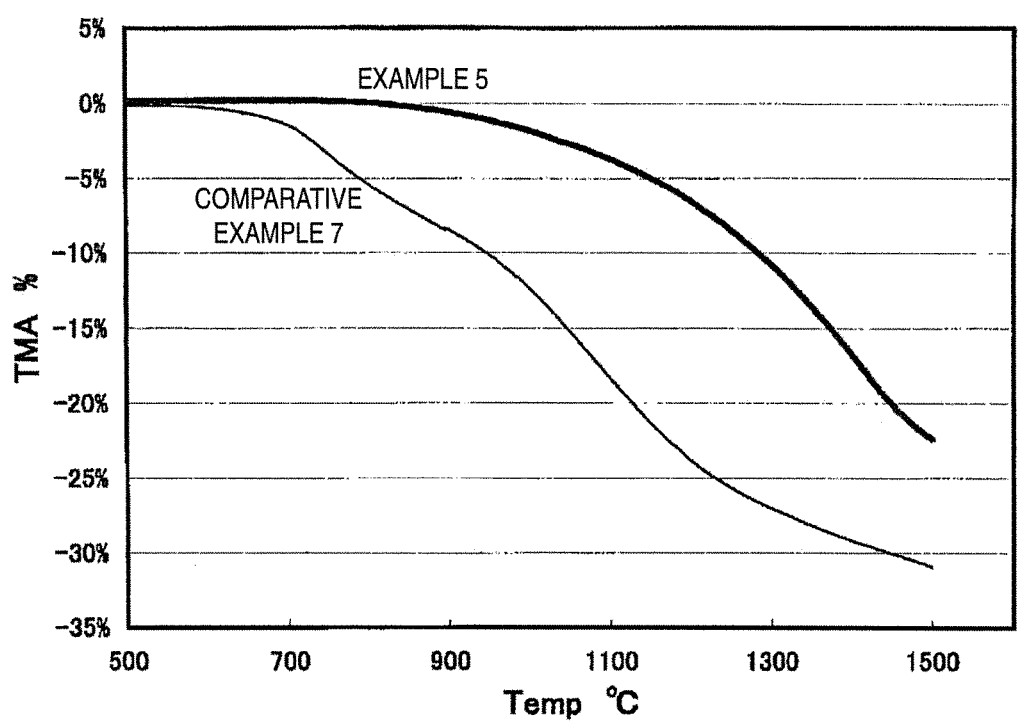
FIG. 6 is a TMA curve illustrating thermal shrinkage of metal pastes according to whether particle diameter adjustment is performed or not (Example 5, Comparative Example 7).

On the other hand, referring to FIG. 5 which is the measurement result of electric conductivity (the electrode resistance relative to the platinum weight per unit area) in view of the activity as the gas sensor electrode, the resistance per unit area is high and the activity is low when the mixing amount of the ceramics is low (Comparative Examples 4, 5). In contrast, the activity becomes preferable from around a level where the mixing amount of the ceramic exceeds 5 mass %. However, when the mixing amount of the ceramic is 25 mass %, electrical conduction is lost, and therefore, the measurement cannot be performed. The difference in the results between these Example and Comparaparticles has a meaning of obtaining an electrode having a porous structure by appropriately setting the sintering timing thereof, and more specifically, a meaning of ensuring the electrode activity. In addition, there is also another significant meaning, which is to appropriately set the shrinkage rate during the metal paste firing in order to prevent the substrate from being deformed or broken. Therefore, thermomechanical analysis (TMA) is performed on the metal paste of Example 5. As the measurement condition of this examination, the temperature raising rate was set to 20° C./min while a load of 1 g was applied to a sample of φ5 mm under atmosphere. The shrinkage curve (TMA curve) which is a result thereof is shown in FIG. 6. Note that this measurement is also applied to the metal paste having 10 wt % of $ZrO_2$ mixed in the conductive particles not having been subjected to the particle diameter adjustment based on the thermal treatment (this will be referred to as Comparative Example 7).

As can be seen from FIG. 6, the metal paste having the ceramic powder mixed in the conductive particles not having been subjected to the particle diameter adjustment in Comparative Example 7 indicates a significant change in the shrinkage rate at a temperature higher than 750° C. which is a shrinkage temperature (a temperature at which 5% shrinkage occurs with respect to 400° C. where the organic component is lost). When the metal paste is applied to the substrate and fired, it is highly possible that the substrate would be broken, for example. In contrast, in the metal paste having been subjected to the particle diameter adjustment, the shrinkage temperature is high (1150° C.), and the shrinkage curve is relatively mild. Therefore, it can be said that by appropriately setting the firing temperature, the electrode film can be formed without deforming or breaking the substrate.

INDUSTRIAL APPLICABILITY

According to the present invention, a porous electrode film can be formed while conductive metal and ceramic particles are dispersed in a fine state. The present invention is preferable for a metal paste for forming a gas sensor electrode of a gas sensor such as an NOx sensor and an oxygen gas sensor electrode, and in addition, the electrode film can be made thin. Therefore, the costs of various kinds of sensor devices can be reduced.

The invention claimed is:

1. A metal paste for forming a gas sensor electrode, in which (1) a conductive particle having a core/shell structure comprising a core particle made of Pt or Pt alloy and a shell made of ceramic covering at least a portion of the core particle, and (2) ceramic powder, are dispersed in a solvent,
   wherein the conductive particle is a particle of which average particle diameter is 90 to 500 nm, and the core particle is covered with ceramic of 0.5 to 3.0 mass % with respect to the mass of the conductive particle,
   a content of the ceramic powder is 5 to 20 mass % with respect to a total mass of the conductive particle and the ceramic powder,
   a total content of a ceramic component in a metal paste is 6.0 to 22.0 mass % with respect to the total mass of the conductive particle and the ceramic powder, and
   further, a dispersion degree measured according to a line transect method based on a grind gauge is equal to or less than 15 μm.

2. The metal paste for forming the gas sensor electrode according to claim 1, wherein the particle diameter of the ceramic powder is 100 to 500 nm.

3. The metal paste for forming the gas sensor electrode according to claim 2, wherein the ceramic acting as the shell and the ceramic powder comprise ceramic including $ZrO_2$.

4. The metal paste for forming the gas sensor electrode according to claim 2, wherein the core particle comprises any of Pt or Pt—Pd alloy including Pd of 30 mass % or less.

5. A manufacturing method for a gas sensor electrode, wherein the metal paste for forming the gas sensor electrode according to claim 2 is applied to a substrate, and is fired at 1300 to 1600° C.

6. The metal paste for forming the gas sensor electrode according to claim 1, wherein the ceramic acting as the shell and the ceramic powder comprise ceramic including $ZrO_2$.

7. The metal paste for forming the gas sensor electrode according to claim 6, wherein the core particle comprises any of Pt or Pt—Pd alloy including Pd of 30 mass % or less.

8. A manufacturing method for the metal paste for forming the gas sensor electrode according to claim 6, comprising the steps of:
   making mixed powder by mixing a composite particle having a core/shell structure made of a precious metal particle made of Pt or Pt alloy and a shell made of ceramic covering at least a portion of the core particle and ceramic powder;
   heating the mixed powder to 700 to 1200° C., adjusting a particle diameter of the composite particle, and forming the conductive particles having the core/shell structure of which average particle diameter is 90 to 500 nm; and
   dispersing the mixed powder having been subjected to the thermal treatment into a solvent.

9. A manufacturing method for a gas sensor electrode, wherein the metal paste for forming the gas sensor electrode according to claim 6 is applied to a substrate, and is fired at 1300 to 1600° C.

10. The metal paste for forming the gas sensor electrode according to claim 1, wherein the core particle comprises any of Pt or Pt—Pd alloy including Pd of 30 mass % or less.

11. A manufacturing method for the metal paste for forming the gas sensor electrode according to claim 10, comprising the steps of:
   making mixed powder by mixing a composite particle having a core/shell structure made of a precious metal particle made of Pt or Pt alloy and a shell made of ceramic covering at least a portion of the core particle and ceramic powder;
   heating the mixed powder to 700 to 1200° C., adjusting a particle diameter of the composite particle, and forming the conductive particles having the core/shell structure of which average particle diameter is 90 to 500 nm; and
   dispersing the mixed powder having been subjected to the thermal treatment into a solvent.

12. A manufacturing method for a gas sensor electrode, wherein the metal paste for forming the gas sensor electrode according to claim 1 is applied to a substrate, and is fired at 1300 to 1600° C.

13. A manufacturing method for the metal paste for forming the gas sensor electrode according to claim 1, comprising the steps of:
   making mixed powder by mixing a composite particle having a core/shell structure made of a precious metal particle made of Pt or Pt alloy and a shell made of ceramic covering at least a portion of the core particle and ceramic powder;
   heating the mixed powder to 700 to 1200° C., adjusting a particle diameter of the composite particle, and forming the conductive particles having the core/shell structure of which average particle diameter is 90 to 500 nm; and
   dispersing the mixed powder having been subjected to the thermal treatment into a solvent.

14. The manufacturing method for the metal paste according to claim 13, wherein the average particle diameter of the composite particle is 10 to 25 nm.

15. A manufacturing method for the metal paste for forming the gas sensor electrode according to claim 2, comprising the steps of:
   making mixed powder by mixing a composite particle having a core/shell structure made of a precious metal particle made of Pt or Pt alloy and a shell made of ceramic covering at least a portion of the core particle and ceramic powder;
   heating the mixed powder to 700 to 1200° C., adjusting a particle diameter of the composite particle, and forming the conductive particles having the core/shell structure of which average particle diameter is 90 to 500 nm; and
   dispersing the mixed powder having been subjected to the thermal treatment into a solvent.

* * * * *